United States Patent [19]
Wo

[11] Patent Number: 5,932,244
[45] Date of Patent: Aug. 3, 1999

[54] LIPOSOMAL HUMAN CALCITONIN GENE-RELATED PEPTIDE COMPOSITION AND PREPARATION OF THE SAME

[76] Inventor: Weihan Wo, Halleiner Landesstrasse 106, A-5412 Puch, Salzburg, Austria

[21] Appl. No.: 08/978,875

[22] Filed: Nov. 26, 1997

[30] Foreign Application Priority Data

Nov. 29, 1996 [CN] China .............................. 96-1-20902.X
Oct. 17, 1997 [CN] China .............................. 97-1-19060.7

[51] Int. Cl.$^6$ .................................................. A61K 9/127
[52] U.S. Cl. ........................... 424/450; 424/460; 514/929
[58] Field of Search .................................. 424/450, 460; 530/307; 514/2, 929

[56] References Cited

U.S. PATENT DOCUMENTS

| | | | |
|---|---|---|---|
| 4,515,736 | 5/1985 | Deamer | 264/4.3 |
| 5,374,618 | 12/1994 | Craig et al. | 514/12 |
| 5,631,394 | 5/1997 | Wei et al. | 556/404 |
| 5,693,622 | 12/1997 | Wolff et al. | 514/44 |

*Primary Examiner*—Thurman K. Page
*Assistant Examiner*—Lakshmi Channavajjala
*Attorney, Agent, or Firm*—Watson Cole Grindle Watson, P.L.L.C.

[57] ABSTRACT

The present invention provides a pharmaceutical composition of hCGRP and the preparation of the same. The composition comprises liposomes from nature soybean phospholipid, in which the weight ratio of hCGRP to soybean phospholipid is 1–2 to 100–8000. The half-life of the composition is longer than 72 hours, and the stability of the composition is also enlongated. The composition can be administrated intravenous infusion, oral, nasal mucosal spray in an amount of 0.1–10 pg hCGRP per kg body weigh to treat hypertension and congestive heart failure of a human. The bioavailability of approximately 80%.

13 Claims, No Drawings

LIPOSOMAL HUMAN CALCITONIN GENE-RELATED PEPTIDE COMPOSITION AND PREPARATION OF THE SAME

BACKGROUND OF THE INVENTION

This invention relates to liposomal complex of human calcitonin gene-related peptide (liposomal hCGRP) composition and the preparation of the same, in particular to a product obtained by combining phospholipid and hCGRP.

Human α-type calcitonin gene-related peptide (hCGRP) is an endogenous neuromodulator and is the most potent vasodilator known to date. Its a marketable product which can be purchased throughout the world. However, hCGRP, as shown in other peptides, is unstable in storage (in vitro, aqueous solution) and circulation (in vivo) with half-life of 9–12 min, and it is difficult to use such peptide as a drug for clinical application.

The object of the invention is to provide a liposomal hCGRP which can be used as a clinical drug, and to provide a method of production whereby novel phospholipids are associated with hCGRP to obtain a very stable and effective product This liposomal hCGRP can release hCGRP gradually from the liposome to achieve a long-term effect with half-life of 72 min in vivo, which can be effective to prevent and cure cardiovascular diseases.

DESCRIPTION OF THE INVENTION

The present invention relates to a pharmaceutical including of hCGRP comprising liposomes prepared from nature soybean phospholipid. It is characterized in that the weight ratio of hCGRP to soybean phospholipid is 1–2 to 100–8000 (w/w), specially 1.5–2 to 2500–6000 (w/w).

A pharmaceutical composition of liposomal hCGRP containing 20–2000 pg hCGRP in 5 ml of the composition is more preferred.

Mannitol, sorbitol, isotonic saline and dextrose or other pharmaceutically acceptable materials can be added to the pharmaceutical composition of liposomal hCGRP.

The present invention also relates to a method for preparing the pharmaceutical composition of the liposomal hCGRP characterized by the steps of:

(1) adding sterilized and distilled water to purify and dry soybean phospholipid, a with weight ratio of lipid to water greater than 1 to 1000, followed by sonicating to obtain small and single-membrane vesicles of lipid bilayer;

(2) mixing hCGRP, dissolved in $H_2O$ with a ratio of peptide to $H_2O$ in 1 to 1000–25000, with the above soybean phospholipid in a ratio of the peptide to lipid of 1–2 to 100–8000, more particularly 1.5–2 to 2500–6000, sonicatiing and incubating at 37° C. for 30–60 min to obtain a stable composition of liposomal hCGRP.

The composition of liposomal hCGRP thus obtained can be further lyophilized and then dissolved in $H_2O$ to obtain an aqueous solution containing 20–2000 pg hCGRP per 5 ml solution.

The present invention also relates to a method for treating hypertension and congestive heart failure in a human by administering to the patient the aforementioned pharmaceutical composition of liposomal hCGRP. The method includes intravenous infusion, oral, nasal mucosal spray. Among them, intravenous dose of liposomal hCGRP is 0.1–10 pg hCGRP per kg body weight. The bioavailability of liposomal hCGRP is approximately 80%.

Detailed illustration is shown in the following.

Theoritical Basis of Preparation of Liposomal Complex of hCGRP

Composition and sequence of the amino acids of hCGRP are characterized by (1) 8 of 37 amino acids of hCGRP are polar amino acids, with the hydrophilic side chains, and 16 of 37 amino acids are apolar with hydrophobic side chains; (2) 4 of 8 polar amino acids are basic amino acids with positive charges in $H_2O$, and pI of hCGRP is 10. One molecule hCGRP contains 2 arginine, 2 lysine (Lys) and 1 aspartic acid (Asp). Arg and Lys are charged positively, Asp is charged negatively at physiological pH. hCGRP in which the ratio $(\Sigma Lys+\Sigma Arg)/(\Sigma Glu+\Sigma Asp)=4$, is a very strong basic peptide. In physiological pH hCGRP is positively charged by net 3 positive charges. hCGRP contains 16 hydrophobic amino acid and 6 hydrophilic amino acid, and is a very typical amphilic molocule.

By analysis of phospholipid composition, specially soybean phospholipid it has been indicated that (1) acidic lipid with negative charges in head groups in $H_2O$ are above 40% of total phospholipid, (2)unsaturated fatty acid in soybean phosphglycerides are approx 70%, with protection effect from oxidation and hydrolyzation, (3) at the limit of very low lipid concentration (lipid:$H_2O$<1:100 w/w), the thermodynamically stable state is the dispersion of single walled vesicles of soybean phospholipid bilayers. The vesicle size range is 20–50 nm.

In the present invention by thin layer chromatography and gas-phase chromatography the soybean phospholipid components were analysed, corrected and quantified with standard phospholipids (Sigma). The soybean phospholipid used for clinical injection contains 44.9% acidic phospholipids including phosphatidylserine (17.2%), phosphatidylglycerol (8.1%), phosphatidylinositl (15.2%) and cardiolipin (4.4%) with rich negative charges in $H_2O$, and linoleic acid (58.31%), palmitic acid (24.36%), linolenic acid (7.32%), oleic acid (5.9%) and stearic acid (3.88%) with 71.53% unsaturated fatty acid and saturated fatty acid (28.47%). Liposome structure, as noted earlier, are formed spontaneously in $H_2O$ by phospholipid molecules, from many different phospholipids, and the composition most frequently used has been the natural phospholipid extracted from cell membrane, such as soybean phospholipid [Imperial Chemical Industrial Ltd. and National Research Development Corporation, British Patent 1523965 1977]. Small single membrane liposomes range in diameter from approx. 200 Å to 500 Å, and consist of a single lipid bimolecular layer surrounding an aqueous compartment. Small single membrane liposomes are characterized by (1) osmotically insensitive (2) about 70% of the total lipid is located in the outer leaflet of the vesicle (3) at the limit of very low lipid concentration, the thermodynamically stable state is the dispersion of singlemembrane vesicles of lipid bilayer [Gruler H. Microstructure and transport properties of single shelled vesicles and monolayers of lipid mixtures and lipid/protein alloyes, in Liposomes Drugs and Immunocompetent Cell Functions. Edited by Claude Nicolau 1981.99 15–27] (4) medium to large liposomes (MLV and LUV) are cleared rapidly from circulation after i.v. administration, small unilamellar liposomes offer the potential for sustained drug release in a blood stream and targeting to tissues other than the reticuloendthelial cell. The great emphasis is placed upon liposome as a biomembrane model, creating some possibility of in vivo application in medicine and research [Yang F. Y., The Application of Liposome in The Research in Biomembrane and Pharmacology, SHENWUHUAXUE YU SHENGWUWULI JINZHAN (*Biochemistry And Biophysics*, 1977 6:36]. Soybean phospholipid is a novel lipid existing in biomembrane, which have been used for preparation of artificial membranes, such as liposomes [Biomembrane Group, Institute of Biophysics, Chinese Academy of Sciences, SHENWUHUAXUE YU SHENG-WUWULI JINZHAN (*Biochemistry And Biophysics*, 1978 4:1].

By sonication and incubation the possibility presents itself for the polar interaction of the negatively charged groups of the phospholipid with the positively charged groups of the amino acid resides of hCGRP on the outer surface of the membrane by ionic bonding with $H_2O$. The apolar groups are located in hydrophobic area of membrane by hydrophobic force, including tails of phospholipid and hydrophobic amino acid residues from hCGRP. The thermodynamic stability of liposomal hCGRP has been achieved with increase of half-life from 9–12 to 72 min and long-term storage in aqueous solution for two years (orginal storage time of 15 days). The effective dose of only $10^{-5}$ liposomal hCGRP represents a remarkable reduction in dosage and furthermore it can be absorbed by mucasal administration including oral, nasal and rectum mucosa with bioavailability of 80% approx. Clinical studies indicated that remarkable treatment effect of liposomal hCGRP on 200 patients with hypertension and congestive heart failure had been achieved, and no secondary effect had been observed.

EXAMPLE 1

Preparation of liposome from soybean phospholipid 25 g soybean phospholipid was rotary evaporated (by using rotary evaporater, XZ-6, produced by Zhongkeyuan Kelong Corp.) from a chloroform:methanol (2:1,v/v) solution to form a thin film in golden on the walls of a 1000 ml round bottomed flask.

After the last obvious traces of solvent had been removed, rotary evaporating was continued for 15 min, followed by drying for a further 15 min under a nitrogen atmosphere. The lipid was suspended in 250 ml of distilled water by shaking with a few glass beads by using a shaker (HZS-D, produced by Harbin Donglian Corp.) and then by a sonicator (DF-6P3c, produced by Ningbo Xinyi Research Institute) for 30 min.

Reconstitution of hCGRP in liposome membrane 10 mg hCGRP was desolved in 250 ml distilled water, and stirred for 5 min. hCGRP solution was mixed with the above liposome solution (250 ml), stirred for 5 min, and sonicated for 2–3 min, three times with interval of 3–5 min (by using a sonicator, DF-6P3c, produced by Ningbo Xinyi Research Institute). Then the mixture was incubated at 37° C. for 40 min (by using a bath sonicator, produced by Harbin Donglian Corp.).

Sedimentation of liposomal hCGRP

The restituted solution was Sedimented by Ultracentrifage (400000×g, for 40 min, at 4° C., VAC 602, WEB Lipzig, Germany) and washed with distilled water by three times.

Lyophilization and Resolution

The sedimented liposomal hCGRP was lyophilized by using lyophilizer LGJ (produced by Instrument Plant of Academy of Military Medical Sciences (China)) and dissolved in distilled water (passed through 6# sterilizing filter) (lipid:$H_2O$=1:1000 w/w), the above solution was sterilized at 100° C. for 30 min, and enclosed.

EXAMPLE 2

The procedure of Example 1 was repeated except by using various ratio of peptide to lipid (w/w). hCGRP reconstitution in membrane, the reconstitution efficiency and the stability of the final product were compared, as shown in Table 1.

TABLE 1

Effect of Liposomal hCGRP with various ratio of peptide to lipid (w/w) in preparation procedure on the reconstitution efficiency and vasodilatory activity.

| Ratio of hCGRP to lipid (w/w) | Free hCGRP (%) | Relative Vesodilatory activity (%) |
|---|---|---|
| 1:1 | 80.2 ± 10.1% | 0.02 ± 0.01% |
| 1:10 | 24.5 ± 3.6% | 1.2 ± 0.3% |
| 1:100 | 15.7 ± 1.9% | 32.6 ± 6.7% |
| 1:1000 | 0.1 ± 0.02% | 95.1 ± 11.4% |
| 1:10000 | 0.1 ± 0.03% | 94.9 ± 13.9% |
| 1:250000000 | 0 ± 0% | 100 ± 0% |

Method: liposomal hCGRP was prepared according to the precedure of Example 1 with various ratios of peptide to lipid (w/w), followed by centrifugating and determining of hCGRP content in supernate as free hCGRP not reconstituted in the membrane. After that each group of samples was divided into two groups, one was stored at −70° C. after being sterilized and enclosed under nitrogen as control, and another was dissolved in $H_2O$ with the ratio of lipid to $H_2O$ in 1 to 1000 (w /w) stored in room temperature after being sterilized and enclosed. After a storage time of 24 months vasodilatory activity of the samples were measured, shown as % of control. Each date is mean±SD of five independent data.

In Table 1 it is seen that when the ratio of lipid to peptide was above 1000 (w/w), hCGRP had been reconstituted in membrane with little free hCGRP, and vasodilatory activity remained at above 95% after 24-month-storage.

EXAMPLE 3

In the following test, a similar procedure to that of Example 1 was repeated except by using different ionic strength to study the effect of ionic strength in solution on reconstitution efficiency of hCGRP in lipid membrane. Table 2 lists the effect of ionic strength on hCGRP reconstitution.

TABLE 2 the effect of ionic strength in solution on reconstitution effeciency of hCGRP in lipid membrane.

| NaCl Conc. (mM) | 0 | 10 | 50 | 100 | 150 |
|---|---|---|---|---|---|
| Free hCGRP | 0.2 ± 0.1% | 11.6 ± 1.8% | 24.5 ± 4.2% | 35.5 ± 7.9% | 36.1 ± 4.1% |

Method: In NaCl agueous solution with different concentrations, hCGRP was reconstituted in soybean phospholipid membrane, followed by centrifugating and determination of free hCGRP content in supernatant liquid, shown as % of total hCGRP. The ratio of peptide to lipid was 1 to 1000 (w/w), each datum was mean ±SD of five independent experimental data.

In Table 2, it is indicated that the reconstitution efficiency decreased with increasing of ionic strength in solution. The purified $H_2O$ solution may offer a favorable environment for interaction and association between lipid and peptide.

COMPARATIVE EXAMPLE 1

The same procedure of Example 1 was repeated except by using two non-charged lipids instead of soybean phospholipid.

By determination of free hCGRP content in supernatant liquid after centrifugation and chromatographic analysis, it was shown that the reconstitution efficiency of hCGRP in soybean phospholipid membrane achieved 99.9%, but in PC and PE membrane were only 21.2% and 30.3% respectively, indicating that negative charge of phospholipid is very important to reconstitute hCGRP in membrane successfully.

TABLE 3

Comparison of reconstitution efficiency of hCGRP in soybean phopholipid (SP), phophatidylcholine (PC), and phosphatidylethnolamine (PE) membrane (%).

| Sample | Kd | % | Kd | % |
|---|---|---|---|---|
| hCGRP | 0.52 | 100% | 0.04 | 0% |
| hCGRP + PC | 0.52 | 79.8% | 0.04 | 21.2% |
| hCGRP + PE | 0.52 | 69.3% | 0.04 | 30.3% |
| hCGRP + SP | 0.52 | 0.1% | 0.04 | 99.9% |

COMPARATIVE EXAMPLE 2

Three different phospholipids including soybean phospholipid (SP), phosphatidylcholine (PC) and phosphotidylethnolamin (PE) were used for liposomal hCGRP preparation, and the structure integrity of hCGRP in three liposome membrane was analyzed during 24-month storage by HPLC, as shown in Table 4.

Method: hCGRP in sample was extracted with acid solution and analyzed by reverse phase HPLC, retention time and peak area of hCGRP during chromatography were recorded. Each datum is mean ±SD of five independent experimental date. hCGRP standard (BACHEM, Swizerland) was used for correction of retention time.

Results in Table 4 indicated that little change of hCGRP purity was observed during 24-month storage with decrease of 1.4%, indicating that hCGRP renconstituted in soybean phospholipid membrane is very stable during storage, but in PE and PC membrane are unstable and integrity of hCGRP remained only 64.4% and 65.1%.

COMPARATIVE EXAMPLE 3

In the following test, phosphatidylcholine (PC) and phosphetidylethnolamin (PE) were used for liposome-hCGRP perparation and compared with soybean phopholipid liposomal hCGRP. During 24-month storage vasodilatory activities of three various liposomal hCGRP were determined and compared as shown in Table 5.

TABLE 4

Effect of various phospholipid on integrity of hCGRP reconstituted in lipid membrane

| | time (months) | | | | | | | | |
|---|---|---|---|---|---|---|---|---|---|
| | 0 | 3 | 6 | 9 | 12 | 15 | 18 | 21 | 24 |
| SP (% area) | 98.4 ± 2.4 | 98.4 ± 2.1 | 99.0 ± 1.9 | 98.0 ± 2.4 | 97.8 ± 2.1 | 97.8 ± 2.0 | 97.1 ± 1.8 | 97.1 ± 1.9 | 97.0 ± 1.7 |
| PC (% area) | 99.2 ± 3.3 | 90.2 ± 2.9 | 83.3 ± 3.4 | 76.4 ± 3.1 | 70.1 ± 2.6 | 68.2 ± 2.5 | 66.1 ± 1.9 | 65.8 ± 2.0 | 65.1 ± 1.9 |
| PE (% area) | 98.9 ± 2.9 | 94.5 ± 3.1 | 89.2 ± 2.2 | 85.3 ± 3.3 | 82.1 ± 1.9 | 76.6 ± 1.7 | 70.3 ± 1.6 | 68.5 ± 2.1 | 64.4 ± 2.2 |

TABLE 5

Effect of various phospholipid on vasodilation of hCGRP reconstituted in lipid membrane ($ED_{50}$ values × $10^{-8}$ mg/ml)

| | storage (months) | | | | | | | | |
|---|---|---|---|---|---|---|---|---|---|
| Samples | 0 | 3 | 6 | 9 | 12 | 15 | 18 | 21 | 24 |
| Control (at − 70° C., n = 5) | | | | | | | | | |
| mean ± SD | 4.7 ± 0.6 | 4.9 ± 0.5 | 5.2 ± 0.7 | 5.1 ± 0.8 | 5.3 ± 0.5 | 5.2 ± 0.7 | 5.1 ± 0.6 | 5.2 ± 0.6 | 5.3 ± 0.7 |
| PS in H$_2$O (at 25° C., n = 5) | | | | | | | | | |
| mean ± SD | 5.1 ± 0.7 | 4.9 ± 0.8 | 4.9 ± 0.9 | 5.3 ± 0.7 | 5.5 ± 0.6 | 5.2 ± 0.7 | 5.5 ± 0.8 | 5.6 ± 0.6 | 5.9 ± 0.8 |
| PC in H$_2$O (at 25° C., n = 5) | | | | | | | | | |
| mean ± SD | 4.9 ± 0.8 | 15.2 ± 3.2 | 50.6 ± 10.3 | 151 ± 21.2 | 451 ± 99.3 | 865 ± 153 | 1133 ± 333 | 1566 ± 439 | 1923 ± 544 |
| PE in H$_2$O (at 25° C., n = 5) | | | | | | | | | |
| mean ± SD | 5.2 ± 0.7 | 10.3 ± 2.4 | 33.4 ± 6.5 | 99.1 ± 15.8 | 329 ± 82.8 | 634 ± 101 | 903 ± 125 | 1234 ± 289 | 1633 ± 345 |

Methods: Experiments were performed on New Zealand white rabbits (weight 2.5–3.5 kg) that were anesthetized with pentobarbital sodium (30 mg/ kg, i.v.).

Rabbits were placed in a headholer, diameters of ocular vesselsl (conductive) were measured by use of a microscope equipped with a TV camera coupled a video monitor. Images were recorded in computer and vessel diameters were measured later with an image analyzer software. The analytic systems of microcirculation was purcharged from DAHENG Co. China. 10 μl of diluted samples was dropped into the eye of the rabbits and the images of ocular vessels were recorded in the computer.

During storage of 24 months $ED_{50}$ values ($\times 10^{-18}$ mg/ml) for vasodilation of liposomal hCGRP were determined. Little changes in soybean phospholipid membrane of liposomal hCGPR were observed. But, for PC and PE liposomal hCGRP, their $ED_{50}$ were decreased 100–1000 folds after 24-month storage, indicating negative charges in the lipid membrane is very important for stable association between the peptide with lipid.

Experiment 1

Analysis of hCGRP-liposome complex

Methods: Liposomal hCGRP and free hCGRP were analyzied by the method of Berk [Berk D. and Marcinka K., Gel Chromatography in Separation Methods. Deylz ed. 1984, 271]. hCGRP samples reconstituted with or without soybean phospholipid (1.0 ml in 0.1M Tris-HCl, pH8.8) were applied to a 1.5×46 cm sephdex G-50 fine column in 0.1M Tris-HCl, pH8.8. Blue dextran 2000 (Pharmacia) and $^{32}PO_4$ (England) were mixed with separated sample as mark of Vo and Vi respectively.

Free hCGRP in Sehadex G-50 fine was chromatography at Kd=0.52, but liposomal hCGRP Kd=0.44, similar to blue dextron 2000, indicating that the liposome-hCGRP complex had been fomed. The data obtained by gel filtration were described in Table 5.

TABLE 6

Determination of hCGRP binding with soybean phospholipid

| | Kd (G-50) | | |
|---|---|---|---|
| hCGRP | 0.52 | 0.54 | 0.51 |
| hCGRP + Lipid | 0.04 | 0.04 | 0.05 |
| Blue Dextran 2000 | 0 | | |
| $^{32}PO_4$ | 1 | | |

Each datum represented individual experiment result.

As shown in Table 6, after the reconstitution of hCGRP with soybean phospholid, much more large complex of hCGRP with lipid than hCGRP had been formed, indicating that the properties of hCGRP and soybean phospholipid give a new light on the preparation of a stable liposomal hCGRP.

Experiment 2

Analysis of physical and chemical stability of liposomal hCGRP

It is clearly that any liposomal formulation must have adequate stability over the time period between its preparation and ultimate use so as to be a pharmaceutical carrier. The surface of liposome membrane, as mentioned above, has large amounts of negative charges, which prevents change of their size induced via the fusion between liposomes. In an environment of large amount of water, the negative charged particles is in a thermodynamic stable state and large amount of unsaturated tails in phospholipid can reduce posibility of water molecule inserting into lipid bilayer to prevent degradation of lipid and peptide molecules from auto-hydrolysis and auto-oxidation.

Phospholipids are subject to hydrolysis in agueous media, resulting initially in the formation of the corresponding lysophospholipid and fatty acid. During the storage of our liposome or liposomal hCGRP, the contents of lyophospholipid were determinated as a criteria of chemical stability by TLC, while the size of liposome was measured by gel filtration observing the position of elution peak as a criteria of physical stability [Szoka F., et al., Comparative properties and methods of preparation of lipid vesicles (liposomes), Ann. Rev. Biophys. Bioeng. 1980 9:467.5].

Analysis LPC Content

Changes of LPC content in soybean phospholipid liposome. Storage conditions: at 25° C., samples in $H_2O$ Lipid: $H_2O$=1:1000 (w/w) with sterilized at 100° C. for 30 min and enclosed.

Methods: Analysis of LPC content in the liposome was done by TLC. Silica gel H (Type 60) from E, Merk in Germany. LPC standard was purcharged from Sigma, as control of LPC in samples, and its Rf value is 0.04 in our experimental conditions. After samples were sterilized in 100° C. for 30 min, the chemical stability of liposome membrane wes determined by analysis of LPC content at interval of 3 monthes during storage. Every datum is mean ±SD of 5 independent TLC (i.e., n=5). The mixture of the samples and standard LPC was used for corrective assay by single direction TLC and double direction TLC, indicating that LPC of the mixture was only one component on the silica gel.

During storage period of 24 months, the content of LPC was increased progressively from 2.1±0.34% to 4.7±0.51% (p<0.01) for soybean phospholipid vesicles and from 1.9±0.22% to 3.4±0.46% (p<0.01) for the liposomal hCGRP, respectively. The degradation percentages of phospholipid molecules were 2.6% and 1.5% for liposome and liposomal hCGRP respectively, indicating that the reconstituted hCGRP can increase stability of membrane by its positively charged groups which interact with negatively charged groups of phospholipid.

Determination of liposome size was carried out by means of gel filtration (Kd) during storage period. Kd values were unchanged either for soybean phospholipid liposome or for the reconstituted liposome with hCGRP, indicating that our liposomes are thermodynamically stable in 1000:1 ($H_2O$: phospholipid, w/w) environment during 24 months storage after sterilization.

Experiment 3

Analysis of the stabilities of hCGRP rconstituted in liposome membrane

Stability of hCGRP reconstituted in liposome membrane was observed by (A) Sephadex G-50 fine gel filtration to measure the dissociation of hCGRP from the liposome; (B) microcirculation observation system to see the vasodilatory activity, and in comparison with free hCGRP during storage period.

A. The stability of association of hCGRP with membrane (Table 8).

Methods: During storage period of the reconstituted liposome after being sterilized at 100° C. for 30 min, free hCGRP, dissociated from the liposome, was determined by gel filtration at the interval of 3 months. The absorption at UV 206 nm of hCGRP has been correlated with 0.52 of the distribution coefficient (Kd) in correction of hCGRP standard. At this Kd value, we can investigate whether hCGRP is dissociated from the reconstituted liposome during storage period. Sephadex G-50 fine gel filtration was carried out, every datum is mean±SD of 3 indepentent operations.

During the storage period of 24 months the hCGRP reconstituted in the liposome membrane was not dissociated into free hCGRP by observation of absorption (at 206 nm) of eluent solution at Kd=0.52. This result shows us that hCGRP can form a very stable complex with soybean phospholipid vesicles by our experimental procedure based on the characteristics of their molecular sturcture. All samples were stored at 25° C. after sterilized and enclosed. The ratio of lipid: $H_2O$ is 1:1000 in the reconstituted liposome of soybean phopholipid.

B. Measurement of vasodilatory activities of hCGRP hCGRP is an endogenous neuromodulator and the most powerful vasodiatator known by us. We investigated vasodilatory activities of hCGRP reconstituted in the liposome membrane of soybean phospholipid and in comparison with free hCGRP in $H_2O$ and human plasma during storage period.

In $H_2O$, the vasoditatory activities (diameter %) of free hCGRP and hCGRP reconstituted in liposome membrane of soybean phospholipid were altered from +187±8.9% to +83±12.4% (p<0.001, n=5) and from +198±16.4 to +196±14.3% respectively after storage period of 90 days. In human plasma, their activities decreased from +195±16.49% to +25±6.8% (p<0.001, n=5) and from +198±19.2% to +184±6.1% respectively after incubation for 48th. These results indicated that the reconstituted hCGRP in the liposome menbrane is more stable in comparision with free hCGRP.

Treatment Experiment 1

Role of liposomal hCGRP in treatment of patients with congestive heart failure (CHF)

Patients: The human studies were carried out in sixteen patients admitted for the control of congestive heart failure: seven were male and nine female, with an average age of 66.3 years (range 54 to 75). Six in New York Heart Association (NYHA) phase IV, seven in phase III and three in phase II [Bruce R. A. Mod. Concepts Cardiovasc. Dis. 1956, 25:321–326]. All patients were treated with liposomal hCGRP after stopping of treatment with other drug such as digoxin for three days.

TABLE 7

Comparison of vasodilation of hCGRP reconstituted in the liposome membrane of soybean phospholipid and free hCGRP.

A. in $H_2O$, 25° C.

| | hCGRP | | | | Liposome-hCGRP | | | |
|---|---|---|---|---|---|---|---|---|
| day | 0 | 30 | 60 | 90 | 0 | 30 | 60 | 90 |
| 1 | +189 | +142 | +94 | +82 | +191 | +189 | +192 | +201 |
| 2 | +191 | +133 | +99 | +79 | +193 | +194 | +190 | +191 |
| 3 | +181 | +152 | +84 | +63 | +184 | +186 | +188 | +181 |
| 4 | +192 | +161 | +99 | +88 | +199 | +202 | +198 | +200 |
| 5 | +179 | +165 | +114 | +102 | +221 | +219 | +221 | +209 |
| mean ± SD | +187 (8.9) | +151 (14.2) | +98 (9.2) | +83 (12.4) | +198 (16.4) | +198 (13.2) | +198 (12.7) | +196 (14.3) |

B. in plasma, 37° C.

| | hCGRP | | | | Liposome-hCGRP | | | |
|---|---|---|---|---|---|---|---|---|
| hour | 0 | 12 | 24 | 48 | 0 | 12 | 24 | 48 |
| 1 | +213 | +102 | +52 | +29 | +197 | +191 | +193 | +190 |
| 2 | +191 | +93 | +49 | +33 | +223 | +190 | +194 | +189 |
| 3 | +187 | +114 | +79 | +22 | +186 | +187 | +185 | +181 |
| 4 | +194 | +90 | +82 | +19 | +187 | +185 | +186 | +179 |
| 5 | +188 | +87 | +51 | +24 | +195 | +192 | +193 | +183 |
| mean ± SD | +195 (16.9) | +97 (14.4) | +63 (16.7) | +25 (6.8) | +198 (19.2) | +189 (12.3) | +190 (7.2) | +184 (6.1) |

Methods: Experiments were performed on New Zealand white rabbits (weight 2.5–3.5 kg) that were anesthetized with pentobarbital sodium (30 mg/kg, i.v.). Rabbits were placed in a headholer, diameters of ocular vessels (conjictive) were measured by use of a microscope equipped with a TV camera coupled a video monitor. Images were recorded in computer and vessel diameters were measured later with an image analyzer software. The analytic systems of microcirculation was purchased from DAHENG Co. China. 10 μl of diluted samples was dropped into the eye of the rabbits and the images of ocular vessels were recorded in a computer. The vessel diameter of the images was analyzed by the microcirculation software.

Drugs: Liposomal hCGRP, prepared by Example 1, was used for treatment of the patients, containing 20 pg hCGRP/5 ml solution. Drug content is 2000 BU/5 ml.

Dose administration route:

Mucosal absorption: via oral-nasal mucosal 40–80 BU (1–3 drops) three times per day; via anus2000 BU 3 times per day;

Intraveneous infusion: 2000–8000 BU (2–4 ampoules) of Liposomal hCGRP added to 5% GS or 100–250 ml 0.9% NaCl solution. 1 time per day.

Measurement: Before and after the drug breathing rate, vesicular sound, heart rate and rhythm, liver size, swelling index, weight, urinary volume, and cordiac performance by means of ECG, Echocardiography were observed and measured per day.

Result: Liposomal-hCGRP had sustained beneficial effects on patients with CHF. Most patients felt symptomatically better the next morning. There were a dominant cardiac improvement in 9 patients, effective in 6, only one remained unchanged. No subject complained of side-effect to drug such as headache, flushing. The drug caused no hypotension and did not affect the liver or renal function during treatment.

TABLE 8

Treatment effect of liposomal hCGRP on patients with congestive heart failure

| Patient No. | Pre-drug | OD | Days | Effeciency DE | E | ND |
|---|---|---|---|---|---|---|
| 1. CO intoxication | III | i.n | 1 | | II | |
| 2. PCD | IV | i.n | 1 | | III | |
| 3. CO intoxication | III | i.n | 1 | | II | |
| 4. CAD | II | i.n | 7 | | | II |
| 5. HCD | II | i.n | 7 | | I | |
| 6. SCD | IV | i.v | 7 | I | | |
| 7. MI | IV | i.v | 7 | | II | |
| 8. MD | III | i.v | 7 | I | | |
| 9. MD | III | i.v | 7 | I | | |
| 10. MD | IV | i.v | 7 | | III | |
| 11. MD | III | i.v | 7 | I | | |
| 12. HCD | III | i.v | 7 | I | | |
| 13. HCD | IV | i.v | 7 | II | | |
| 14. HCD | IV | i.v | 7 | | II | |
| 15. HCD | IV | i.v | 7 | II | | |
| 16. HCD | III | i.v | 7 | I | | |

*i.n: nasal mucosal administration; i.v: intravenous administration; PCD: Pulmonary cardiac disease; CAD: Coronary artery desease; HCD: Hypertensive cardiac disease; MI: Myocardial infarction; MP: Myocardial disease; DE: Dominant effeciency; E: Effeciency; MD: No difference.

Discussion: Congestive heart failure (CHF) is usually caused by reduced cardiac output as a result of impaired myocardial contractivity, improvement of which is a importent object of treatment in patients with CHF. Calcitonin gene related peptide (CGRP) is a neuropeptide with potent vasodilation and positive chronotropic and inotropic action on the heart, indicating that it may be used for CHF treatment The recent studies have proved that intravenous infusion of CGRP (8.0 ng/kg/min) for 8 h caused a decrease in the right arterial, pulmanary artery, pulmonary artery wedge and systemic arterial pressure.

Cardiac output, stroke volcemt, and renal blood flow and glomerular filtration increased. Application of liposomal hCGRP in this invention to 16 CHF patients has obtained beneficial effects, and was charaterized by the following:

(1) hCGRP release gradually from liposomes with long-term effect, average effective time of 10 hours, equal to 5 fold of the results of hCGRP reported in other investigations;

(2) easy absorption via mucosa, such as oral, nasal and anus adminstration;

(3) bioavailability of liposomal hCGRP being 10 fold than that of hCGRP reported in other investigations.

Treatment Experiment 2

Role of liposomal hCGRP in treatment of patients with essential hypentesion

Materials and Method:

Patients: Twenty one of hospitalized patients with essetial hypertension, ten male and eleven female, average age of 62.2 years (range 45 to 73 ), 1 had aldosteronism. Their hypertension ranged from 3 to 37 years, their clinical information had given clear diagnosis. According to WHO/ISH 1993 hypertension diagnosis standard (Beijing Renmin Weigheng Chubanshe 1996, 227–228), patients in phase hypertension were 11,in III hypertension 10.

Drugs and Measurement Sixteen patients stopped administration of other hypotensive drugs for two weeks, five patients obtained little hypotension treated with mepramidil and carvedilol. Liposomal hCGRP, prepared in Example 1, was used for all patients by means of i.v infusion or oral-nasal mucosal administration.

a. Oral-nasal mucosal: 0.05–0.10 ml liposome-hCGRP, containing 0.2–0.4 pg hCGRP, was given three times per day and for five consecutive days.

b. Intravenous infusion: one ampoule of liposome-hCGRP, containing 20 pg hCGRP in 5 ml aqueous solution, was given in 100–500 ml 0.9% NaCl per day and for five consecutive days.

c. Measurement: Artery blood pressure (BP) was measured at 15, 30, 60, 120, 180 min after adminstration on the first day. During following days, BP were recorded 6 times in pre- and post-drug per day.

Determination of hypotension:

According the diagnosis standard of 1979 cerdiavascular epidemiology (Henan, Zhen Zhou, China) [J. Chinses Cardiovascular Diseases 1979 7:(2):18], hypotension of liposomal hCGRP was determined.

Dominant efficacy: diastolic pressure decrease >100 mmHg and to normotensive level, or only >20 mmHg.

Efficacy: diastolic pressure decrease 10 mmHg and to normotensive level, or 10–19 mmHg.

Uneffective: diastolic pressure did not decrease to normotensive level or decrease <10 mmHg.

In patients only with systolic pressure increase, hypotension of drug was determined according to the above standard plus systolic pressure decrease of 20 mmHg.

Results: 21 patients were treated with liposomal hCGRP of the invention, 4 mucosal administration, 4 intravenous infusion, 13 were given combinative adminstration of i.v. with mucosal, 2 via anius mucosa, 2 via oral mucosa, and rest via nasal muscosa.

Treatment result Systolic pressure was decreased 20–105 mmHg, average decreasing of 17 mmHg (p<0.001, n=21).

Diastolic pressure was decreased 5–25 mmHg, average decreasing of 17 mmHg (p<0.001, n=21). Liposomal hCGRP was dominant efficacy for 13 patients, effective for 7 and uneffective for 1. Hypotension began within 5 after administration, and was maintained approx. 10 h.

Secondary effect:

2 patients with chronic nasitis felt a little comfortless by nasal mucosa administation, after i.v. infusion was used, nasal symptom vanished. During treatment with liposomal hCGRP, headache and flushing did not occur, no liver or renal lesions were observed.

Discussion

1. CGRP is indogenous neropeptide. Limpsomal hCGRP in the present invention has avoided rapid degradation of CGRP to achieve long-term effect via gradually releasing hCGRP in vivo, and its is easy to be absorbed by tissue cells. For treatment of hypertension, it affects very fast, effectively and safely. In 21 patients dominant efficacy achieved 61.9%, total effeciency 95.2%, only one was not effective, and no remarkable difference was observed for treatment effeciency of hypertension by either i.v. infusion or mucosal absorption of liposomal hCGRP.

2. Some reports indicated dose-dependent effect of CGRP on hypertension in animal, hypotension effecacy increased with the dose-increase. However, in 21 patients with hypertension in the experiment, optimal hypotension efficacy was observed by 40–80 BU liposomal hCGRP via nasal musosal absorption, further increase of the dose did not obtain better result, which may be caused by increase of cardiac output induced by hCGRP positive inotropic action on heart 3. Shekgar et al. [Shekhar YC, et al., Effects of Prolonged Infusion of Human Alpha Calcitonin Gene-Related Peptide on Hemodynamics, Renal Blood Flow and Hormone Levels in Congestive Heart Failure, Am J Cardiol 1991; 67:733.] reported that i.v. infusion of hCGRP (8.0 ng/kg/min) for 8 h with total dose of 3840 ng/kg induced hypotesion, systemic artery blood pressure decreased 18% ($p<0.05$) 30 min after drug. In this experiment, the hypotensive dose was 8000 BU/ day, and hCGRP content was only 780 pg, i.e., 0.8 pg hCGRP per kg body weight, equal to $2.0\times10^{-7}$ fold of the hCGRP dose reported by other researches.

4. A little secondary effect, only 1 patient felt nasal discomfort after nasal administration, possibly related to nasal vasodilation. Thus patient with nasal disease should be treated by other route of administation of liposomal hCGRP.

What is claimed is:

1. A pharmaceutical composition of hCGRP comprising liposomes from natural soybean phospholipid, in which the ratio of hCGRP to soybean phospholipid is 1–2 to 100–8000, and wherein the hCGRP is incorporated in the phospholipid.

2. A pharmaceutical composition of hCGRP as in claim 1, comprising in that the weight ratio of hCGRP to soybean phospholipid is 1.5–2 to 2500–6000.

3. A pharmaceutical composition of hCGRP as in claim 1, comprising 20–2000 pg hCGRP in 5 ml of said composition.

4. A method for preparing the pharmaceutical composition of hCGRP comprising the steps of:

(1) adding sterilized and distilled water to purified and dried soybean phospholipid in a weight ratio of lipid to water being greater than 1 to 1000, followed by sonificating to obtain small and single-membrane vesicles of lipid bilayer and (2) mixing hCGRP, dissolved in $H_2O$ with the ratio of peptide to $H_2O$ being 1 to 1000–25000, with the above soybean phospholipid in a peptide to lipid ratio of 1–2 to 100–8000, sonicating and incubating at 37° C. for 30–60 min to obtain a stable composition of liposomal hCGRP.

5. A method as in claim 4, wherein the weight ratio hCGRP to soybean phospholipid is 1.5–2 to 2500–6000.

6. A method as in claim 4, comprising in that further comprising the step of lyophilizing, and then dissolving the liposomal hCGRP in $H_2O$ to obtain an aqueous solution containing 20–20000 pg hCGRP per 5 ml solution.

7. A method for treating hypertension of humans by administrating to the patient one of the pharmaceutical compositions of hCGRP as defined in claim 1, by intravenous infusion, oral, nasal mucosal spray in an amount of 0.1–10 pg hCGRP per kg body weight.

8. A method for treating congestive heart failure of a human by administrating to the patient one of the pharmaceutical compositions of hCGRP as defined in claim 1, by intravenous infusion, oral, nasal mucosal spray in an amount of 0.1–10 pg hCGRP per kg body weight.

9. A method as in claim 5, further comprising the step of lyophilizing, and then resolving the liposomal hCGRP in $H_2O$ to obtain an aqueous solution containing 20–2000 pg hCGRP per 5 ml solution.

10. A method for treating hypertension of a human by administrating to the patient one of the pharmaceutical composition of hCGRP as in claim 2, by intravenous infusion, oral, nasal mucosal spray in an amount of 0.1–10 pg hCGRP per kg body weight.

11. A method for treating hypertension of a human by administrating to the patient one of the pharmaceutical composition of hCGRP as in claim 3, by intravenous infusion, oral, nasal mucosal spray in an amount of 0.1–10 pg hCGRP per kg body weight.

12. A method for treating congestive heart failure of a human by administrating to the patient one of the pharmaceutical composition of hCGRP as in claim 2, by intravenous infusion, oral, nasal mucosal spray in an amount of 0.1–10 pg hCGRP per kg body weight.

13. A method for treating congestive heart failure of a human by administrating to the patient one of the pharmaceutical composition of hCGRP as in claim 3, by intravenous infusion, oral, nasal mucosal spray in an amount of 0.1–10 pg hCGRP per kg body weight.

* * * * *